(12) United States Patent
Tenerz

(10) Patent No.: US 7,021,152 B2
(45) Date of Patent: *Apr. 4, 2006

(54) SENSOR AND GUIDE WIRE ASSEMBLY

(75) Inventor: Lars Tenerz, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 66 days.

This patent is subject to a terminal disclaimer.

(21) Appl. No.: 10/622,136

(22) Filed: Jul. 18, 2003

(65) Prior Publication Data

US 2005/0011272 A1    Jan. 20, 2005

(51) Int. Cl.
*G01L 7/00* (2006.01)

(52) U.S. Cl. ......................................................... 73/756

(58) Field of Classification Search ............... 600/486, 600/488; 73/754, 756, 706; 128/637, 642
See application file for complete search history.

(56) References Cited

U.S. PATENT DOCUMENTS

| | | | |
|---|---|---|---|
| 3,724,274 A | | 4/1973 | Millar |
| 4,274,423 A | | 6/1981 | Mizuno et al. |
| 5,018,529 A | * | 5/1991 | Tenerz et al. ............... 600/480 |
| 5,085,223 A | * | 2/1992 | Lars et al. ................... 600/488 |
| 5,113,868 A | * | 5/1992 | Wise et al. .................. 600/488 |
| 5,125,058 A | * | 6/1992 | Tenerz et al. ................. 385/66 |
| 5,226,423 A | * | 7/1993 | Tenerz et al. ................ 600/486 |
| RE35,648 E | | 11/1997 | Tenerz et al. |
| 6,112,598 A | * | 9/2000 | Tenerz et al. .................. 73/756 |
| 6,142,958 A | * | 11/2000 | Hammarstrom et al. ..... 600/585 |
| 6,167,763 B1 | * | 1/2001 | Tenerz et al. .................. 73/756 |
| 6,336,906 B1 | * | 1/2002 | Hammarstrom et al. ..... 600/585 |
| 2001/0051769 A1 | * | 12/2001 | Hoek et al. .................. 600/381 |

FOREIGN PATENT DOCUMENTS

| | | |
|---|---|---|
| EP | 0 738 495 A1 | 10/1996 |
| EP | 0 888 744 A2 | 1/1999 |

OTHER PUBLICATIONS

U.S. Appl. No. 10/611,661, filed Jul. 2, 2003, Tenerz et al.

* cited by examiner

*Primary Examiner*—William Oen
*Assistant Examiner*—Andre Allen
(74) *Attorney, Agent, or Firm*—Foley & Lardner LLP

(57) ABSTRACT

A sensor and guide wire assembly (21) for intravascular measurements of physiological variables in a living body includes a core wire (22; 32) and a sensor element (23; 33). The sensor element (23; 33) includes basically a mounting portion (12; 34), which is mounted to the core wire (22; 32), and a pressure sensitive end portion (25; 35) whose upper side is provided with a pressure sensitive device, such as a membrane (26; 36). A recess (27; 37), which is provided between the mounting portion (24; 34) and the pressure sensitive portion (25; 35), provides the sensor element (23; 33) with an articulated action when the core wire (22; 32) is bent.

19 Claims, 2 Drawing Sheets

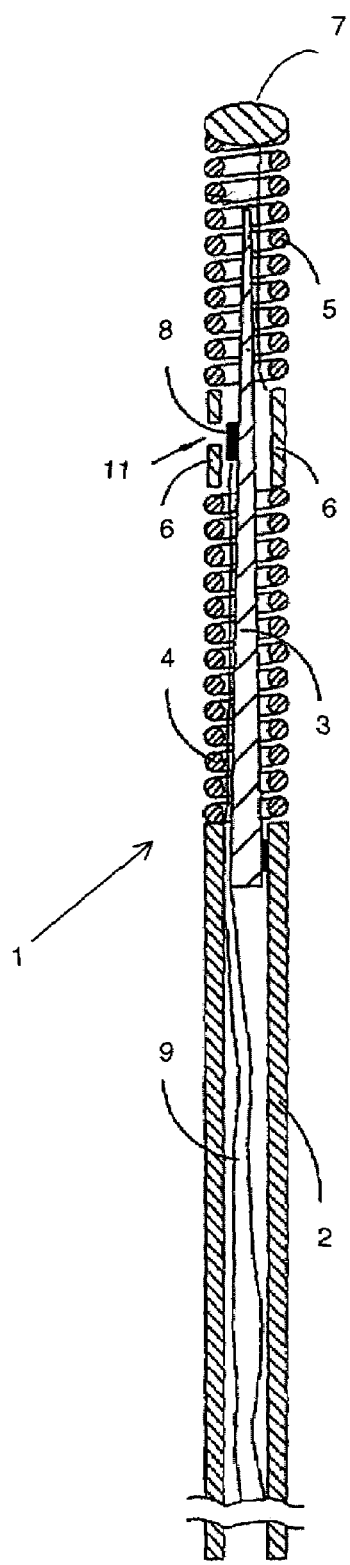
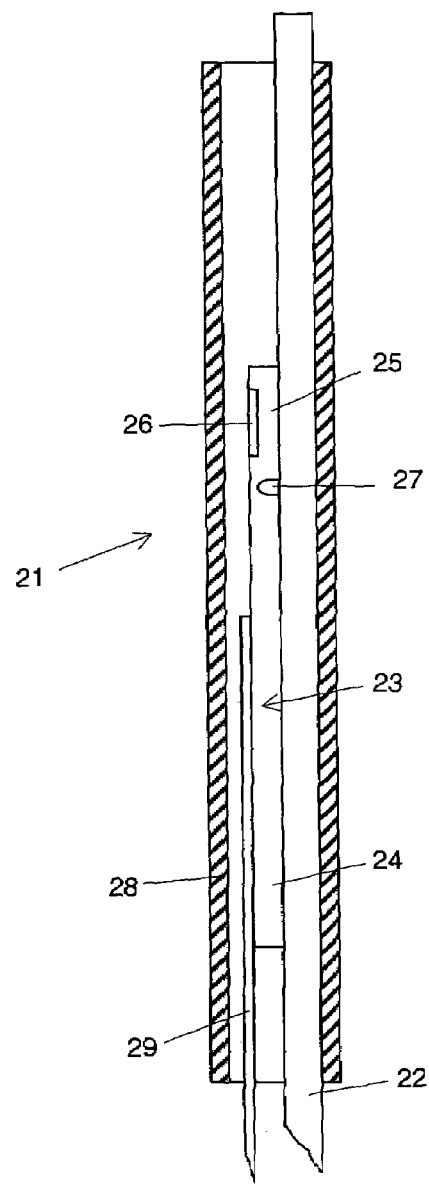
Fig. 1
(Prior Art)
Fig. 2

SENSOR AND GUIDE WIRE ASSEMBLY

FIELD OF THE INVENTION

The present invention relates generally to sensor and guide wire assemblies, in which a sensor element is mounted at the distal end of a guide wire for intravascular measurements of physiological variables in a living body, and in particular to the shape and mounting arrangement of the sensor element.

BACKGROUND OF THE INVENTION

Sensor and guide wire assemblies in which a sensor is mounted at the distal end of a guide wire are known. In U.S. Pat. No. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire (a core wire), and a coil attached to the distal end of the solid wire. The sensor element comprises a pressure sensitive device, e.g. a membrane, with piezoresistive elements connected in a Wheatstone bridge-type of arrangement mounted thereon.

As is recognized in U.S. Pat. Nos. 6,112,598 and 6,167,763, which also are assigned to the present assignee, a potential problem with this kind of guide wire mounted sensors is the occurrence of so-called bending artefacts. A bending artefact is a change in the output signal from the sensor that is induced by a bending of the guide wire, rather than being induced by a change in the physical environment surrounding the sensor. For a sensor and guide wire assembly like the one disclosed in Re. 35,648, this means that when the guide wire is bent, the bending of the guide wire imposes a strain on the sensor element, which thereby is deflected or stretched (or contracted). The deflection of the sensor element is then transferred to a deformation of the pressure sensitive device; and, according to well-known principles, the output from the Wheatstone bridge will thereby be affected by the bending of the guide wire.

According to U.S. Pat. Nos. 6,112,598 and 6,167,763, a solution to this problem is to mount the sensor element in a cantilevering fashion such that the pressure sensitive end of the sensor element does not contact any structure other than its mount. These two patents disclose several embodiments with different ways of mounting the sensor element so that bending forces are not exerted on the pressure sensitive end of the sensor element. A common feature of these embodiments is that an elongated, essentially rectangular sensor chip is mounted in a recess in the core wire in such a way that the proximal end of the chip is attached to the core wire, while the distal end of the sensor chip protrudes into the recess such that a clearance is provided below the distal portion of the chip where the pressure sensitive device (e.g. a membrane) is provided.

In the U.S. application of Lars Tenerz and Mattias Tullberg, entitled "SENSOR AND GUIDE WIRE ASSEMBLY," filed Jul. 2, 2003, U.S. Ser. No. 10/611,661 and which is assigned to the present assignee, a principally different solution is presented. Here it is the design of the sensor element itself—rather than the mounting arrangement and design of the core wire—that provides the resistance against bending artefacts. According to this application, a sensor element comprises a mounting base which provides for the desired cantilevered mounting of the sensor element.

Although a sensor and guide wire assembly provided with a sensor chip designed and mounted according to the teachings of U.S. Pat. Nos. 6,112,598 and 6,167,763 in practise has proven to work well, the design of a sensor and guide wire assembly can be improved, not least from a manufacturing point of view.

SUMMARY OF THE INVENTION

As mentioned above, the sensor element according to the prior art comprises an elongated, essentially rectangular chip with a membrane made from polysilicon provided thereon. To achieve the desired resistance against bending artefacts, this chip can be designed and mounted in different ways, the common feature being that it is the cantilevered mounting arrangement that provides the desired resistance against bending artefacts.

An object of the present invention is to provide a new and improved design for a sensor chip so that, when the sensor chip is mounted in a sensor and guide wire assembly, the sensor and guide wire assembly will have the same or better characteristics regarding resistance against bending artefacts. Preferably, the sensor and guide wire assembly should at the same time be easier and thereby cheaper to manufacture.

These objects are achieved with a sensor chip and a sensor and guide wire assembly according to the present invention.

A sensor and guide wire assembly comprises a sensor element in the form of a generally rectangular and rather thin sensor chip with a pressure sensitive device provided thereon. The pressure sensitive device can be in the form of a membrane, which covers a small cavity in the upper side at a first end portion of the sensor chip and which has piezoresistive elements mounted thereon. According to the invention, a recess is provided at the under side of the sensor chip. This recess, which constitutes a border between the first end portion and a second portion of the sensor chip, provides the sensor chip with a thin portion having less bending resistance than the rest of the chip. When the sensor element is mounted in a sensor and guide wire assembly, with at least the second portion of the sensor chip being attached to a core wire, this thin portion will act as a hinge or articulation when the core wire is bent. By the provision of this hinge, the pressure sensitive portion of the sensor element is not constrained to adapt to bending deformations of the core wire, which prevents such deformations from being transferred to the pressure sensitive device.

Another object of the present invention is to provide a method for manufacturing a sensor chip according to the present invention. Preferably, the sensor chip is made from a single piece of silicon that is etched to the desired shape, including the aforementioned recess.

BRIEF DESCRIPTION OF THE DRAWINGS

FIG. 1 illustrates the general design of a sensor and guide wire assembly according to the prior art.

FIG. 2 illustrates a portion of a sensor and guide wire assembly comprising a sensor chip according to the present invention.

DETAILED DESCRIPTION OF THE INVENTION

Figure 3:
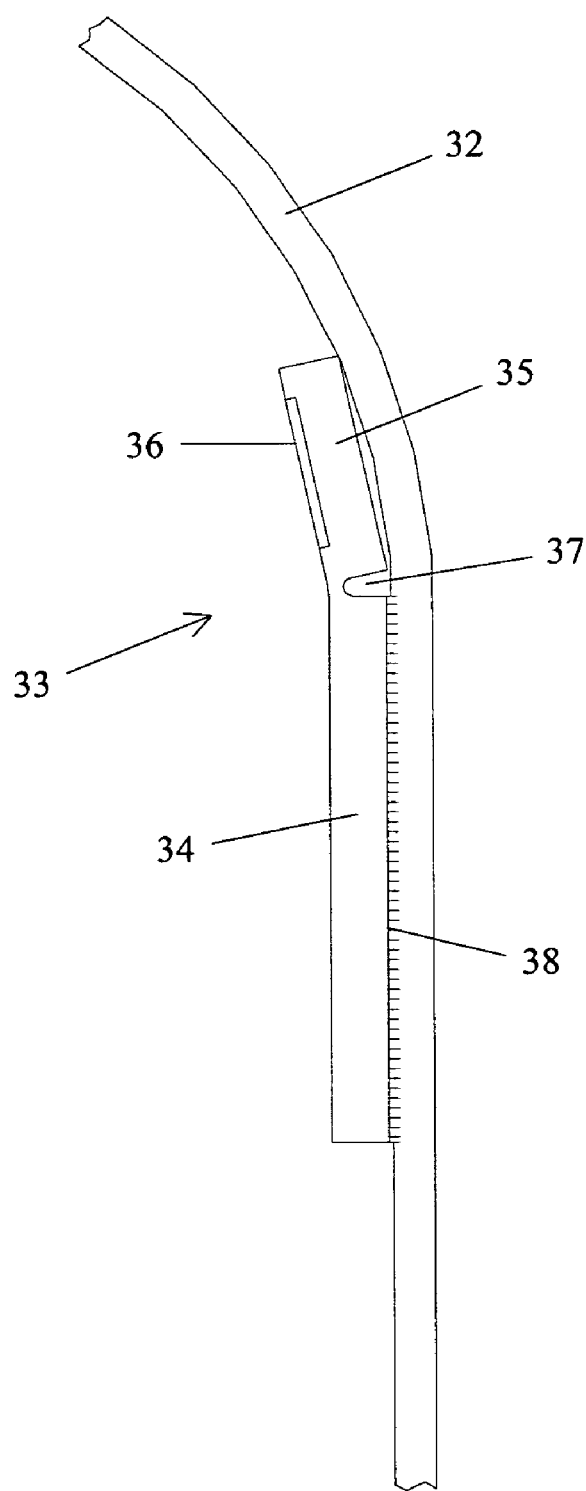
FIG. 3 illustrates schematically the behaviour of a sensor chip according to the present invention during bending of a core wire on which the sensor chip is mounted.

For better understanding of the context in which a sensor chip according to the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element or chip 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane 10 (not visible in the figure), which through an aperture 11 in the jacket 6 is in contact with a medium, such as blood, surrounding the distal portion of the sensor guide 1.

Although not shown in the figure, the sensor element 8 further comprises an electrical circuitry, which in a Wheatstone bridge-type of arrangement is connected to one or several piezoresistive elements provided on the membrane 10. As is well known in the art, a certain pressure exerted on the membrane 10 from the surrounding medium will thereby correspond to a certain stretching of the membrane 10 and thereby to a certain resistance of the piezoresistive elements mounted thereon and, in turn, to a certain output from the sensor element 8. It should therefore be clear that it is highly preferable that this output from the sensor element 8 does not change due to factors that are not related to a real change in the physical properties of the surrounding medium. As was mentioned above, one such factor is so-called bending artefacts, the source of which is that a bending of the sensor guide 1 is transferred to a deformation of the membrane 10. Here, the discussion above about piezoresistive elements coupled in Wheatstone bridge-type of arrangement should only be seen as an illustrative exemplification; in short, the basic problem is that a pressure sensitive device, such as a membrane, can be influenced by a bending of a sensor guide.

To remedy the potentially adverse effects from bending artefacts, the present invention provides a new design of a sensor chip to be used in a sensor and guide wire assembly. FIG. 2 shows a portion of a sensor and guide wire assembly 21 comprising a core wire 22 and a sensor element or chip 23 according to the present invention. The sensor chip 23 comprises essentially two portions, a mounting portion 24, which is attached to the core wire 22, and a pressure sensitive portion 25, on the upper side of which a pressure sensitive device in the form of a membrane 26 is provided. A recess 27, which is provided in the under side of the sensor chip 23, separates partly the mounting portion 24 from the pressure sensitive portion 25. The sensor element 23 is disposed inside a jacket or sleeve 28, and is through at least one electrical lead 29 in contact with an electronic unit (not shown in the figure). The mounting portion 24 can be attached to the core wire 22 by means of gluing. For reasons to be discussed below, the term "mounting portion" should, however, not be interpreted exclusively; in fact, also the pressure sensitive portion of a sensor chip can be attached to a core wire.

FIG. 3 is a schematic illustration of a sensor chip 33 according to the invention. The sensor chip 33 comprises a mounting portion 34, which is attached to a core wire 32 by means of an adhesive 38, and a pressure sensitive portion 35, on the upper side of which a pressure sensitive device in the form of a membrane 36 is provided. A recess 37, which is provided in the under side of the sensor chip 33, constitutes a border between the mounting portion 34 and the pressure sensitive portion 35. At the position of the recess 37, a thin portion remains, such that the sensor chip 33 has a thinner cross section at this position than at the other positions of the sensor chip 33. The bending resistance of this thin portion is less than the bending resistances of the other portions of the sensor chip 33. During introduction of a sensor and guide wire assembly in small and tortuous vessels, the core wire is frequently bent, and in FIG. 3 the core wire 32 is shown in such a bent state. From the simplified picture shown in FIG. 3, it should therefore be clear that when the core wire 32 is bent, the thin portion acts as a hinge between the mounting portion 34 and the pressure sensitive portion 35. Because of this articulated action of the sensor chip 33, the pressure sensitive portion 35 is not forced to adapt to bending deformations of the core wire 32, i.e. the pressure sensitive portion 35 does not have to follow the curvature of the core wire 32. Deformations caused by bending of the core wire 32 will thereby not be transferred to deformations of the pressure sensitive portion 35 and the membrane 36, respectively.

According to the invention, a pressure sensitive device, such as a membrane, should preferably be located rather close to an end of a sensor chip, and the longitudinal distance between the pressure sensitive device and a recess should be small, so that the pressure sensitive portion becomes rather short. In other words, by the provision of a recess, the effective length of a pressure sensitive portion has actually been reduced, which in itself makes the sensor chip less sensitive to bending artefacts. (To understand this statement, one can imagine that if the length of the sensor chip would be infinitely small, the sensor chip, when attached to a core wire by a soft adhesive, would not at all conform to any deformations of the core wire, and would thereby be practically insensitive to bending artefacts.) This last feature is valid also when the pressure sensitive portion is attached to a core wire. It is therefore contemplated that the pressure sensitive portion as well as the mounting portion of a sensor chip can be attached to a core wire. Preferably, a soft adhesive, such as silicone, should be used.

As an example, the total length of a sensor chip according to the invention can be about 1 mm, the width could be about 150 µm, and the thickness of the chip could be about 150 µm. A suitable depth of a recess provided somewhere in the middle of the chip could then be about 50 µm.

Further, although not shown in the figures, the sensor chips described above can comprise piezoresistive elements coupled in a Wheatstone bridge, with one part of the bridge being connected to a membrane and the other part of the bridge being connected to the chip surface outside the membrane. With such an arrangement, the sensor chip is a piezoresistive pressure transducer in that a certain pressure in the medium surrounding the sensor chip corresponds to a certain deformation of the membrane and, in turn, to a certain resistance of the Wheatstone bridge. The output signals from the pressure transducer will thereby reflect the pressure in the medium surrounding the sensor.

According to the invention a new design of a sensor chip is provided. The sensor chip is adapted to be mounted on a core wire, which is a part of a sensor and guide wire assembly. The invention relates thereby also to a new and improved design for a sensor and guide wire assembly, which has improved sensor chip characteristics especially regarding resistance against bending artefacts. Preferably, the sensor chip is made from a single piece of silicon that is etched to the desired shape, including the aforementioned recess. With the new design of the sensor chip, the design of the core wire can be simplified, e.g. the core wire has not to be provided with mounting structures like recesses, which, in turn, lowers the total production costs for the sensor and guide wire assembly as a whole.

Although the present invention has been described with reference to specific embodiments, also shown in the appended drawings, it will be apparent for those skilled in the art that many variations and modifications can be done within the scope of the invention as described in the specification and defined with reference to the claims below. For example, features described above in this patent specification may be combined with features set forth in U.S. Pat. Nos. Re. 35,648; 6,112,598; and 6,167,763 and the U.S. application entitled "SENSOR AND GUIDE WIRE ASSEMBLY" (cited above). The entire contents of these four documents are thus incorporated herein by reference. It should in particular be noted that the improved characteristics of a sensor guide provided with a sensor chip according to the invention are not dependent on the design of the other parts of the sensor guide. Therefore, a sensor and guide wire assembly may or may not include parts like jackets or sleeves, coils and tips with special shapes. Furthermore, the core wire, on which the sensor chip is mounted, may extend along essentially all the length of the sensor guide, or the core wire may only be provided at the distal portion of the sensor guide. It is also contemplated that more than one recess is provided, and the recess(es) could be provided at the same side of the sensor chip as the pressure sensitive device.

What is claimed is:

1. A sensor chip adapted for a sensor and guide wire assembly for intravascular measurement of at least one physiological variable in a living body, wherein the sensor chip comprises a first end portion, a first side of which is provided with a pressure sensitive device, and a hinge portion provided between the first end portion and a second portion of the sensor chip.

2. A sensor chip according to claim 1, wherein the hinge portion comprises an area of reduced cross-sectional area.

3. A sensor chip according to claim 1, wherein the sensor chip is adapted to be mounted on a core wire.

4. A sensor chip for a sensor and guide wire assembly for intravascular measurement of at least one physiological variable in a living body, which sensor chip is adapted to be mounted on a core wire and has a first end portion, a first side of which is provided with a pressure sensitive device, wherein the sensor chip comprises a recess, which is provided between the first end portion and a second portion of the sensor chip.

5. A sensor chip according to claim 4, wherein the recess is provided at the side that is opposite to the side of the sensor chip where the pressure sensitive device is provided.

6. A sensor chip according to claim 4, wherein the pressure sensitive device is provided close to the first end of the sensor chip.

7. A sensor chip according to claim 4, wherein the recess longitudinally is provided close to the pressure sensitive device.

8. A sensor chip according to claim 4, wherein the depth of the recess is about $1/3$ of the thickness of the sensor chip.

9. A sensor chip according to claim 4, wherein several recesses are provided.

10. A sensor chip according to claim 4, wherein the sensor chip is a piezoresistive pressure transducer.

11. A sensor and guide wire assembly for intravascular measurement of at least one physiological variable in a living body, comprising a core wire and a sensor element having a first end portion, a first side of which is provided with a pressure sensitive device, wherein the sensor element comprises a recess, which is provided between the first end portion and a second portion of the sensor element.

12. A sensor and guide wire assembly according to claim 11, wherein the recess is provided at the side that is opposite to the side of the sensor element where the pressure sensitive device is provided.

13. A sensor and guide wire assembly according to claim 11, wherein the pressure sensitive device is provided close to the first end of the sensor element.

14. A sensor and guide wire assembly according to claim 11, wherein the recess longitudinally is provided close to the pressure sensitive device.

15. A sensor and guide wire assembly according to claim 11, wherein the depth of the recess is about $1/3$ of the thickness of the sensor element.

16. A sensor and guide wire assembly according to claim 11, wherein several recesses are provided.

17. A sensor and guide wire assembly according to claim 11, wherein the second portion of the sensor element is attached to the core wire.

18. A sensor and guide wire assembly according to claim 17, wherein the first end portion of the sensor element is attached to the core wire.

19. A sensor and guide wire assembly according to claim 11, wherein the sensor element is a piezoresistive pressure transducer.

* * * * *